United States Patent

Rohrmann et al.

Patent Number: 5,103,030
Date of Patent: Apr. 7, 1992

[54] PROCESS FOR THE PREPARATION OF A CHIRAL STEREORIGID METALLOCENE

[75] Inventors: Jürgen Rohrmann, Neufahrn; Wolfgang A. Herrmann, Giggenhausen, both of Fed. Rep. of Germany

[73] Assignee: Hoechst Aktiengesellschaft, Frankfurt am Main, Fed. Rep. of Germany

[21] Appl. No.: 697,903

[22] Filed: Apr. 30, 1991

Related U.S. Application Data

[63] Continuation of Ser. No. 284,918, Dec. 15, 1988, abandoned.

[30] Foreign Application Priority Data

Dec. 18, 1987 [DE] Fed. Rep. of Germany ....... 3742934

[51] Int. Cl.$^5$ ............................................. C07F 7/08
[52] U.S. Cl. ......................................... 556/12; 556/11
[58] Field of Search .................................... 556/11, 12

[56] References Cited

U.S. PATENT DOCUMENTS 4,794,096 12/1988 Ewen ................................. 502/117

FOREIGN PATENT DOCUMENTS 0129368 12/1984 European Pat. Off. .
WO8703604 6/1987 PCT Int'l Appl. .

OTHER PUBLICATIONS

Marechal, E. et al., *Compt. Rend. Hebdom. Seance L'Acad. Sci.*, 267:Series C, 467–470 (1968).
*Gmelin Hanbuch der Anorganischen Chemie*, 8th Ed., Part 2, Springer-Verlag, Berlin, 1980, pp. 223–232.
Wild et al., "J. Organometall. Chem.", 288, pp. 63–67 (1985).
Ewen et al., "J.A.C.S.", 109, pp. 6544–6565 (1982).
Ewen et al., "Transition Metals and Organometallics as Catalysts for Olefin Polymerization", Kaminsky et al. (Ed.), Proceedings of 9187 Symposium.

Primary Examiner—Paul F. Shaver

[57] ABSTRACT

A chiral, stereorigid metallocene compound of the formula I $$[R^1R^2Si(indenyl)2]Y^2X \quad (I)$$

(me$^2$ = Ti, Zr or Hf)

which is produced as a virtually pure racemate and can be used as a catalyst component for the polymerization of 1-olefins is obtained by reacting a silylindenyl compound of the formula II $$[R^1R^2Si(indenyl)_2]Me_2^1 \quad (II)$$

(Me$^1$ = alkali metal)
with a titanium, zirconium or hafnium tetrahalide.

15 Claims, No Drawings

PROCESS FOR THE PREPARATION OF A CHIRAL STEREORIGID METALLOCENE

This is a continuation of our copending application Ser. No. 07/284,918, filed Dec. 15, 1988, and now abandoned.

The present invention relates to a process for the preparation of chiral, stererorigid metallocene compounds of titanium, zirconium and hafnium.

Together with specific cocatalysts, such as, for example, aluminoxanes, chiral, stereorigid metallocene compounds are highly active stereospecific catalysts for the preparation of high isotactic polypropylene. The chiral compounds may be employed in this application as a racemate, but must not be in the meso form since this form does not exhibit stereospcificity.

There is interest in using a compound of the type [(CH$_3$)$_2$Si(idenyl)$_2$]ZrCl$_2$ for polymerization of 1-olefins. However, it has hitherto not been possible to obtain a compound of this type in the form of the pure racemate. In all attempts, a mixture with the meso form has always been obtained.

Catalysts which comprize substituted mono-, di- and tri-cyclopentadienyl coordination complexes of transition metal and aluminoxanes are known (cf. EP-A-129368). They are used for the preparation of polyolefins having a defined molecular weight. Nothing is stated in this publication on the preparation of the transition metal complexes.

It has now been found that silyl-bridged metallocene compounds are obtained in virtually pure racemic form if an alkali metal salt of a silylindenyl compound is reacted at low temperature with a titanium, zirconium or hafnium halide.

The invention thus relates to a process for the preparation of a chiral, stereorigid metallocene compound of the formula I

[R$^1$R$^2$Si(indenyl)$_2$]Y$^2$X$_2$     (I)

in which R$^1$ and R$^2$ are identical or different and denot a C$_1$- to C$_{20}$alkyl group, a C$_2$- to C$_{20}$-alkenyl group, a C$_6$- to C$_{20}$-aryl group, a C$_7$- to C$_{20}$-alkylaryl group of a C$_7$- to C$_{20}$-aralkyl group, Y$^2$ is titanium, zirconium or hafnium, and X denotes a halogen atom, which comprizes reacting a compound of the formula (II),

[R$^1$R$^2$si(indenyl)$_2$]Y$_2^1$     (II)

in which R$^1$ and R$^2$ have the abovementioned meaning and Y$^1$ is an alkali metal, with a compound of the formula III

Y$^2$X$_4$     (III)

in which Y$^2$ and X have the abovementioned meaning, at a temperature of from −78° C. to +25° C. in an inert solvent for 10 to 1000 minutes.

For the process according to the invention, a silyl compound of the formula II

[R$^1$R$^2$Si(indenyl)$_2$Y$_2^1$     (II)

is employed. In this formula, Y$^1$ is an alkali metal, preferably lithium. R$^1$ and R$^2$ are identical or different and denote C$_1$- to C$_{20}$-, preferably C$_1$- to C$_6$-alkyl, C$_2$- to C$_{20}$-, preferably C$_2$- to C$_6$-alkenyl, C$_6$- to C$_{20}$- preferably C$_6$- to C$_{12}$-aryl, C$_7$- to C$_{20}$-, preferably C$_7$- to C$_{10}$-alkylaryl, C$_7$- to C$_{20}$-, preferably C$_7$- to C$_{10}$-aralkyl, and , in particular, R$^1$ and R$^2$ denote methyl or phenyl. Li$_2$[(CH$_3$)$_2$Si(indenyl)$_2$] is particularly preferably employed.

The compound of the formula II is reacted with the compound of the formula II

Y$_2$X$_4$     (III)

in which Y$^2$ is titanium, zirconium or hafnium, preferably zirconium or hafnium, and X is a halogen atom, preferably chlorine. These metal halides are used either as such or as solvate complexes, for example with tetrahydrofuran. The solvents must be free from moisture and oxygen.

The reaction is carried out in an inert solvent. Suitable solvents are aromatic hydrocarbons, such as, for example, toluene or xylene, aliphatic hydrocarbons, such as, for example hexane or pentane, or ethers, such as, for example, diethyl ether, tetrahydrofuran or dioxane. Toluene, diethyl ether and tetrahydrofuran are preferably used.

The reaction temperature is 31 78° C. to +25° C., preferably −40° C. to 0° C.

The reaction time is 10 to 1000, preferably 60 to 180, minutes.

The reaction is carried out with stirring and in an inert-gas atmosphere.

The ansa-metallocene compounds of the formula I

[R$^1$R$^2$Si(indenyl)$_2$]Y$^2$X$_2$     (I)

thus obtained in which R$^1$, R$^2$, Y$^2$ and X have the abovementioned meaning, can be recrystallized from aliphatic and aromatic hydrocarbons and etheral or halogen-containing solvents. Mixtures of chloroform and hexane have proven particularly favorable.

The process according to the invention has the advantage that the silyl-bridged metallocene compounds are produced in racemic form and contain very low amounts of the meso form, or none at all. This is of decisive importance, particularly when the complexes are used as catalysts, such as, for example, in the polymerization of α-olefins, since only the racemic form, but not the meso form, exhibits stereoselectively. Whereas, for example, rac-[C$_2$H$_4$(indenyl)$_2$]Ticl$_2$, produces highly isotactic polypropylene, its meso form only produces atactic polymer.

All the operations below were carried out in an inert-gas atmosphere using absolute solvents.

EXAMPLE 1

RAC-[(dimethylsilanediyl)bis(θ$^5$-indenyl]hafnium dichloride (rac-[(CH$_3$)$_2$Si(indenyl)$_2$]HfCl$_2$)

52 cm$^3$ (130 mmol) of a 2.5 M hexane of butyllithium are added slowly at room temperature with water cooling to a solution of 18.2 g (63.2 mmol) of (CH$_3$)$_2$Si(indenyl)$_2$ in 20 cm$^3$ of diethyl ether and 30 cm$^3$ of hexane. The mixture is stirred for approximately a further 2 hours at room temperature, and the colorless precipitate is filtered off via a glass frit. After washing repeatedly with hexane and subsequently drying in an oil-pump vacuum, 20.5 g of a colorless powder which contained about 85% by weight of Li$_2$[(CH$_3$)$_2$Si(indenyl)$_2$] were obtained (etherate complex: 92% of theory.

4.76 g (13.5 mmol) of the dilithium salt were added at −78°60 C. to a suspension of 5.40 g (11.5 mmol) of HfCL$_4$. 2THF in 80 cm$^3$ of diethyl ether. The reaction mixture was allowed to warm slowly to room temperature with stirring, a yellow color rapidly setting in from about −30° C. After 1 hour at room temperature, the solution was filtered through a glass frit. The orange-brown residue was extracted with a total of 30 cm$^3$ of chloroform. The orange solution was concentrated to incipient crystallization. This was completed at 31 35° C. and with addition of hexane. It was possible to isolate a total of 2.0 g (32%) of rac-((CH$_3$)$_2$Si(indenyl)$_2$]HfCl$_2$ in the form of orange-yellow crystals which gradually decompose at a temperature greater than 100° C. $^1$H-NMR spectrum (CDCl$_3$): 700-7.57 (m, 8,arom.-H), 6.81 (d,2$\beta$,C$_5$H$_2$), 6.04 (d,2,$\alpha$-C$_5$H$_2$), 1.11 (s,6,Si(CH$_3$)$_2$).

EXAMPLE 2 rac-[(Dimethylsilanedibyl)bis($\eta^5$-indenyl)]zirconium dichloride (rac-[(CH$_3$)$_2$Si(indenyl)$_2$]ZrCl$_2$)

1.35 g (3.60 mmol) of ZrCl$_4$.2THF and 1.40 g (3.96 mmol) of Li$_2$[CH$_3$)$_2$Si(indenyl)$_2$] were reacted analogously to Example 1 in 40 cm$^3$ of diethyl ether, and the product was worked up. 350 mg (22%) of rac-[(CH$_3$)$_2$Si(indenyl)$_2$]ZrCl$_2$ were obtained as orange crystals which gradually decomposed at a temperature greater than 130° C.

$^1$H-NMR spectrum (CDCl$_3$): 7.04-7.60 (m,8,arom.-H), 6.91 (d,2,$\beta$-C$_5$H$_2$), 6.08 (d,2,$\beta$-C$_5$H$_2$) 1.12 (s,6,Si(CH$_3$)$_2$).

EXAMPLE 3 rac-[(Methylphenylsilianediyl)bis($\eta^5$-indenyl)]hafnium dichloride (rac-[(CH$_3$)(C$_6$H$_5$)Si(indenyl)$_2$[HfCL$_2$)

12 cm$^3$ (30 mmol) of a 2.5 M hexane solution of butyllithium were added slowly at room temperature with water cooling to a solution of 4.60 g (13.12 mmol) of (CH$_3$)(C$_6$H$_5$)Si(indenyl)$_2$, prepared from idenyllithium and methylphenyldichlorosilane, in 10 cm$^3$ of diethyl ether and 20 cm$^3$ of hexane. The mixture was stirred at room temperature for a further 30 minutes, and the solvent was removed under reduced pressure. The pale brown residue was dried at 40° C. in an oil-pump vacuum and taken up in 30 cm$^3$ of hexane. The brownish suspension was filtered through a glass frit. The pale brown residue was washed with hexane and dried in an oil-pump vacuum. 5.25 g of a beige powder which contained 90% by weight of Li$_2$[(CH$_3$)(C$_6$H$_5$)Si(indenyl)$_2$] were obtained (etherate complex: 99% of theory). 5.25 g (13.0 mol) of the diliethio salt were added at −78° C. to a suspension of 5.10 g (11.0 mmol) of HfCl$_4$.2THF in 100 cm$^3$ of diethyl ether. The reaction mixture was allowed to warm to room temperature over the course of 10 hours and was filtered through a glass frit. The red-brown residue was washed with 60 cm$^3$ of diethyl ether. The combined orange-yellow filtrates were evaporated to dryness under reduced pressure. The orange-yellow residue remaining was taken up in toluene. After filtration and evaporation in vacuo, 3.1 g (47% of theory) of rac-[(CH$_3$)(C$_6$H$_5$)Si(indenyl)$_2$]HfCL$_2$ were obtained as a yellow powder.

$^1$H NMR spectrum (CDCl$_3$): 6.6-8.1 (m,13,arom-.OH), 6.8-6.9 (m,2,$\beta$-C$_5$H$_2$), 6.10 and 6.16 (2xd,2,$\alpha$C$_5$H$_2$), 1.21 (s,3,SiCH$_3$).

EXAMPLE 4

15.5 cm$^3$ (38.7 mmol) of a 2.5 M hexane solution of butyllithium were added slowly at room temperature with water cooling to a solution of 5.60 g (19.4 mmol) of (CH$_3$)$_2$Si(indenyl)$_2$ in 100 cm$^3$ of THF, a dark-red coloration setting in. After stirring at room temperature for 30 minutes, the dilithio salt solution prepared in this way was added dropwise at 0° C. over the course of 6 hours to a suspension of 7.20 g (19.0 mmol) of ZrCl$_4$.2THF. The batach was concentrated to incipient crystallization, stirred for a further two hours and cooled to −35° C. the orange-precipitate was filtered off on a glass frit and recystallized from chloroform. 1.50 g (17% of theory of rac-[(CH$_3$)$_2$Si(indenyl)$_2$]ZrCl$_2$ were obtained as orange crystals.

We claim:

1. A process for the preparation of a chiral, stereorigid metallocene compound of the formula I

[R$^1$R$^2$Si(indenyl)$_2$]Y$^2$X$_2$     (I)

in which R$^1$ and R$^2$ are identical or different and denote a C$_1$- to C$_{20}$-alkyl group, a C$_2$- to C$_{20}$-alkenyl group, a C$_6$- to C$_{20}$- aryl group, a C$_7$- to C$_{20}$- alkylaryl group or a C$_7$- to C$_{20}$-aralkyl group, Y$^2$ is titanium, zirconium or hafnium, and X denotes a halogen atom, which comprises reacting a compound of formula II

[R$^1$R$^2$Si(indenyl)$_2$]Y$_2^1$     (II)

in which R$^1$ and R$^2$ have the abovementioned meansing and Y$^1$ is an alkali metal, with a compound of the formula III

Y$^2$X$_4$     (III)

in which Y$^2$ and X have the abovementioned meaning, at a temperature of from −78° C. to 25° C. in an inert solvent for a reaction time ranging from 10 to 1000 minutes, and recovering said compound of formula I from the inert solvent.

2. A chiral, stereorigid metallocene compound, formed by the process of claim 1, of the formula I

[R$^1$R$^2$Si(indenyl)$_2$]Y$^2$X$_2$     (I)

in which R$^1$ and R$^2$ are identical or different and denote a C$_1$- to C$_{20}$- alkyl group, a C$_2$- to C$_{20}$- alkenyl group, a C$_6$- to C$_{20}$- aryl group, a C$_7$- to C$_{20}$- alkylaryl group or a C$_7$- to C$_{20}$- aralkyl group, Y$^2$ is titanium, zirconium or hafnium, and X denotes a halogen atom.

3. The process of claim 1, where said Y$^1$ is lithium, said R$^1$ and R$^2$ denote a C$_1$- to C$_6$- alkyl group, C$_2$- to C$_6$- alkenyl group, C$_6$- to C$_{12}$- aryl group, C$_7$- to C$_{10}$- alkylaryl group, or a C$_7$- to C$_{10}$- aralkyl group.

4. The process of claim 1 wherein said R$^1$ and R$^2$ denote methyl or phenyl.

5. The compound of claim 2, wherein said R$^1$ and R$^2$ denote a C$_1$- to C$_6$- alkyl group, C$_2$- to C$_6$- alkenyl, group, C$_6$- to C$_{12}$-aryl group, C$_7$- to C$_{10}$- alkylaryl group, or a C$_7$- to C$_{10}$- aralkyl group.

6. The compound of claim 2, wherein said R$^1$ and R$^2$ denote a methyl or phenyl.

7. The process of claim 1, wherein said compound of formula II is

[(CH$_3$)$_2$Si(indenyl)$_2$]Li$_2$. 

8. The process of claim 1, wherein said Y$^2$ is zirconium or hafnium and X is chlorine.

9. The compound of claim 1, wherein Y$^2$ is zirconium or hafnium and X is chlorine.

10. The process of claim 1, wherein said temperature is less than 0° C.

11. The process of claim 1, wherein said reaction time ranges from 60 to 180 minutes.

12. The process of claim 1, wherein the major amount of said compound of formula I recovered from the inert solvent is in racemic form.

13. The process of claim 1, wherein said compound of formula I recovered from the inert solvent consists essentially of the racemic form of said compound.

14. The compound of claim 2, wherein a major amount of said compound is in the racemic form.

15. The compound of claim 2, wherein said compound consists essentially of the racemic form of said compound.

* * * * *

UNITED STATES PATENT AND TRADEMARK OFFICE
CERTIFICATE OF CORRECTION

PATENT NO. : 5,103,030                   Page 1 of 3
DATED : April 7, 1992
INVENTOR(S) : Jurgen Rohrmann et al It is certified that error appears in the above-indentified patent and that said Letters Patent is hereby corrected as shown below:

In claim 1, column 4, line 28, "meansing" should read --meaning--.

In claim 9, column 4, line 67, "1" should be --2--.

At line 3, formula I should read:

$$--[R^1R^2Si(indenyl)_2]Y^2X--.$$

At line 4, "me" should read --Y--.

At line 9, formula II should read:

$$--[R^1R^2Si(indenyl)_2]Y_2^1--.$$

At line 10, "Me" should read --Y--.

UNITED STATES PATENT AND TRADEMARK OFFICE
CERTIFICATE OF CORRECTION

PATENT NO. : 5,103,030

DATED : April 7, 1992

INVENTOR(S) : Jurgen Rohrmann et al

It is certified that error appears in the above-indentified patent and that said Letters Patent is hereby corrected as shown below:

At column 1, line 18, "stereospcificity" should read --stereospecificity--.

At column 1, line 43, "denot" should read --denote--.

At column 1, line 45, "of" should read --or--.

At column 2, line 7 "formula II" should read --formula III--.

At column 2, line 9, "$Y_2X_4$" should read --$Y^2X_4$--.

At column 2, line 25, "31 78°" should read -- -78°--.

At column 2, line 47, "stereoselectively" should read --stereoselectivity--.

At column 2, line 55, "$\ominus^5$" should read --$\eta^5$--.

At column 3, line 2, "-78°60" should read -- -78°--.

At column 3, line 10, "31 35°" should read -- -35°--.

At column 3, line 15, "700 - 7.57" should read --7.00 - 7.57--.

UNITED STATES PATENT AND TRADEMARK OFFICE
CERTIFICATE OF CORRECTION

PATENT NO. : 5,103,030
DATED : April 7, 1992
INVENTOR(S) : Jurgen Rohrmann et al It is certified that error appears in the above-indentified patent and that said Letters Patent is hereby corrected as shown below:

At column 3, line 16, "(d, 2ß, $C_5H_2$)" should read --(d, 2, ß-$C_5H_2$)--.

At column 3, line 19, "Dimethylsilanedibyl" should read --Dimethylsilanediyl--.

At column 3, line 21, "[$CH_3$)$_2$Si(indenyl)$_2$]" should read: --[($CH_3$)$_2$Si(indenyl)$_2$]--.

At column 3, line 50, "diliethio" should read --dilithio--.

At column 4, line 7, "batach" should read --batch--.

Signed and Sealed this

Fifteenth Day of November, 1994

Attest:

BRUCE LEHMAN

*Attesting Officer*   *Commissioner of Patents and Trademarks*